US00PP16675P2

(12) United States Plant Patent
Utecht

(10) Patent No.: US PP16,675 P2
(45) Date of Patent: Jun. 20, 2006

(54) ***GERANIUM* PLANT NAMED 'FISWEISS'**

(50) Latin Name: *Pelargonium zonale*
Varietal Denomination: Fisweiss

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 90 days.

(21) Appl. No.: 10/998,663

(22) Filed: Nov. 30, 2004

(51) Int. Cl.
*A01H 5/00* (2006.01)

(52) U.S. Cl. ..... Plt./326
(58) Field of Classification Search ..... Plt./326
See application file for complete search history.

(56) References Cited

PUBLICATIONS

German PBR Application No. PEL 1896 filed Jun. 4, 2003 and withdrawn Oct. 5, 2004 (Copy of German Gazettes dated 1) Jul. 15, 2003—Listing Assigned Application for Protection No. (2 pgs), 2) May 15, 2004—Publishing Proposed Variety Denomination (2 pgs), and 3) Nov. 15, 2004—Listing Withdrawal of Application for Protection (2 pgs)).

Canadian PBR Application No. 03–3903 filed Nov. 21, 2003 (Copy of Canadian Plant Varieties Journal dated Jan., 2004 Listing Assigned Application No. (2 pgs).

Community Plant Variety Office (CPVO) No. 2004/1255 filed Jul 5. 2004 (Copy of Official Gazette of the CPVO dated Oct. 15, 2004 Listing Assigned Application No. and Variety Denomination (3 pgs).

Fischer 2005 catalogue offering 'Fisweiss' (with shipment of plant material available starting Dec., 2004) (3 pgs).

*Primary Examiner*—Kent Bell
(74) *Attorney, Agent, or Firm*—Foley & Lardner LLP

(57) ABSTRACT

A new and distinct cultivar of *geranium* plant named 'Fisweiss' particularly characterized by the combined features of round, white, semi-double flowers; semi-spherically inflorescences; large, medium-green foliage with slight zonation; medium growth habit, with a relatively low, but wide and well-branched plant habit; and an early to mid spring flowering response.

1 Drawing Sheet

Genus and species of the plant claimed: *Pelargonium zonale L'Hèritier* (hybrid).
Variety denomination: 'Fisweiss'.

BACKGROUND OF THE INVENTION

The present invention comprises a new and distinct cultivar of *geranium*, botanically known as *Pelargonium zonale,* and hereinafter referred to by the cultivar name 'Fisweiss'.

'Fisweiss' is a product of a planned breeding program which had the objective of creating improved zonal *geranium* cultivars with white flower color, medium green, possibly zoned foliage, and suitable for the range of medium sized varieties.

'Fisweiss' originated from a hybridization made by the inventor, Angelika Utecht, in a controlled breeding program in Hillscheid, Germany, in 1995. The female parent was an unpatented hybrid plant, no. 92-2074-24, having white, single-type flowers, medium green foliage without or with very faint zonation, and about medium sized plant habit. The male parent of 'Fisweiss' was the patented variety 'Fisalb' (U.S. Plant Pat. No. 9,761), and characterized by white, somewhat zygomorphic flowers, deep green foliage with slight zonation, and relatively compact plant habit.

'Fisweiss' was selected as one flowering plant within the progeny of the stated cross by Angelika Utecht in 1996 in a controlled environment in Galdar, Gran Canaria, Spain.

The first act of asexual reproduction of 'Fiseiss' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from cuttings of the plant initiated in May of 1997, in Hillscheid, Germany, and continuing thereafter, has demonstrated that the combination of characteristics as herein disclosed for 'Fisweiss' are firmly fixed and are retained through successive generations of asexual reproduction.

BRIEF SUMMARY OF THE INVENTION

'Fisweiss' has not bene observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fisweiss' in combination distinguish this *geranium* as a new and distinct cultivar:

1. round, white, semi-double flowers;
2. semi-spherically shaped inflorescences;
3. relatively large, medium-green leaves with slight zonation;
4. about medium sized, rounded and well-branched plant habit; and
5. early to medium spring flowering response.

Of the many commercial cultivars known to the present inventor, the most similar in comparison to 'Fisweiss' is the parental variety 'Fisalb'.

In comparison to 'Fisalb', 'Fisweiss' has a different shape of flowers: the corolla is semi-double and nearly round with the petals mostly overlapping, while flowers of 'Fisalb' are zygomorphic, with a distinct gap between upper and lower petals, and they appear almost single-type due to having only 6 petals on average. Furthermore, 'Fisweiss' has larger umbels and grows somewhat more vigorously.

BRIEF DESCRIPTION OF THE DRAWING

The accompanying photographic drawing shows typical flower and foliage characteristics of 'Fisweiss' with colors being as true as possible with an illustration of this type. The photographic drawing shows a side perspective view of a flowering potted plant of 'Fisweiss' with leaves, buds and inflorescences.

DETAILED BOTANICAL DESCRIPTION

The measurements were taken in Hillscheid, Germany, in mid May, 10 weeks after planting of rooted cuttings. The plants were growing in 14 cm pots, they had not been pinched.

In the following description, color references are made to The Royal Horticultural Society Colour Chart. The color values were determined indoors from plants growing in a green-house in May 2003 in Hillscheid, Germany.

Parentage:
- *Male parent.*—'Fisalb', (U.S. Plant Pat. No. 9,761).
- *Female parent.*—Unpatented, hybrid plant no. 92-2074-24.

Classification: *Pelargonium zonale* L'Héritier (hybrid).

Propagation: Vegetative cuttings.

Inflorescence:

Umbel:
- *Shape.*—Semi-spherical.
- *Average diameter.*—92 mm.
- *Average depth.*—63 mm.
- *Number of flowers per umbel.*—About 20–30.

Peduncle:
- *Peduncle length.*—148 mm.
- *Peduncle diameter.*—4–5 mm.
- *Peduncle color.*—Yellow-green, RHS 144 B.

Pedicel:
- *Pedicel length.*—28 mm in length.
- *Pedicel diameter.*—2 mm.
- *Pedicel color.*—Yellow-green, RHS 144 C.

Corolla:
- *Average diameter.*—48 mm.
- *Depth.*—About 20 mm.
- *Form.*—Semi-double-type.
- *Shape.*—Round outline, with the upper petals about the same size as the lower petals, flat cup-shape, no or only very few inner petals.

Petaloids:
- *Number of petaloids.*—1–3.
- *Length.*—5–15 mm.
- *Width.*—2–7 mm.
- *Overall shape.*—Variable: linear, spatulate or elliptical.
- *Apex shape.*—Pointed (acute) or rounded.
- *Base shape.*—Acute, acuminate, or attenuate.
- *Margin.*—Entire, apart from occasionally occurring notches.
- *Color of upper petaloids.*—Whiter than RHS 155 D.
- *Color of lower petaloids.*—Whiter than RHS 155 D.

Petals:
- *Number of petals.*—5–6.
- *Shape of petals.*—Obovate or round, base acute, upper end is rounded, margin is entire.
- *Size of petals.*—Upper petals: 30–32 mm long, 31–33 mm wide; lower petals: 28 mm long, 32–33 mm wide.
- *Color (general tonality from a distance of three meters).*—Pure white.
- *Color of upper petals.*—Whiter than RHS 155 D (actually as white as the background color of the Colour Charts).
- *Markings of upper petals.*—No markings.
- *Color of lower petals.*—Whiter than RHS 155 D.
- *Markings of lower petals.*—None.
- *Color of lower surface of petals.*—White, RHS 155 C to 155 D.

Sepals:
- *Color of sepals.*—Yellow-green, RHS 144 C, upper and lower surfaces.
- *Number of sepals.*—5.
- *Shape of sepals.*—Linear to lanceolate, acute tip, fused base, surface with very short pubescence, margin entire.
- *Size of sepals.*—13–14 mm long, 4 mm wide for the largest upper sepal, 2–3 mm in width for the other sepals.

Bud (just prior to petals unfolding):
- *Shape.*—Elliptical.
- *Color of sepals.*—Light yellowish-green, RHS 144 C.
- *Color of petals.*—Light yellow-Green, RHS 150 D to white, RHS 155 A.
- *Length.*—22 mm.
- *Width.*—13 mm.

Reproductive organs:
- *Androecium.*—Most often 7 fertile anthers, moderate pollen, orange, RHS N25A, filaments white, RHS 155 D.
- *Gynoecium.*—One pistil, style and stigma white; RHS 155 C to RHS 155 D; 5–6-lobed stigma.
- *Fertility/seed set.*—No seed set observed.

Spring flowering response period: In Hillscheid, Germany, in 2003 plants had on average 0.8 flowers opened 8 weeks after planting of rooted cuttings.

Outdoor flower production: Continuously and rich flowering, the flower count in 2003 in Hillscheid, Germany, indicated about 15 inflorescences per plant in late summer.

Durability: Good stability of flower color, fair rain resistance.

Lastingness of the individual flower: About 7–8 days at 18° C., about 16–18 days for the umbel.

Fragrance: None.

Plant:

Foliage:
- *Shape.*—Kidney-shaped, with cordate base, with the gap between the lowest lobes open, apex rounded with very weak lobes, margin somewhat wavy.
- *Margin.*—Bicrenate.
- *Texture.*—Upper surface smooth, slightly glossy.
- *Size of leaf.*—95 mm wide, 65 mm long.
- *Color of upper surface.*—Medium green, approximately RHS 137 D.

*Color of zonation.*—Very weak, not always visible, green, RHS 137 B.

*Color of lower surface.*—Green, RHS 137 D.

*Petioles.*—50–75 mm long, 2.5–3.0 mm diameter, light green in color, approximately RHS 143 B.

General appearance and form:

*Stem color.*—Light green, RHS 143 C.

*Internode length.*—5 mm.

*Branching pattern.*—8.5 branches.

*Size of plants.*—Height: 12.1 cm, Spread: 26.2 cm (10-week old plants, as described).

I claim:

1. A new and distinct cultivar of *geranium* plant named 'Fisweiss', as described and illustrated herein.

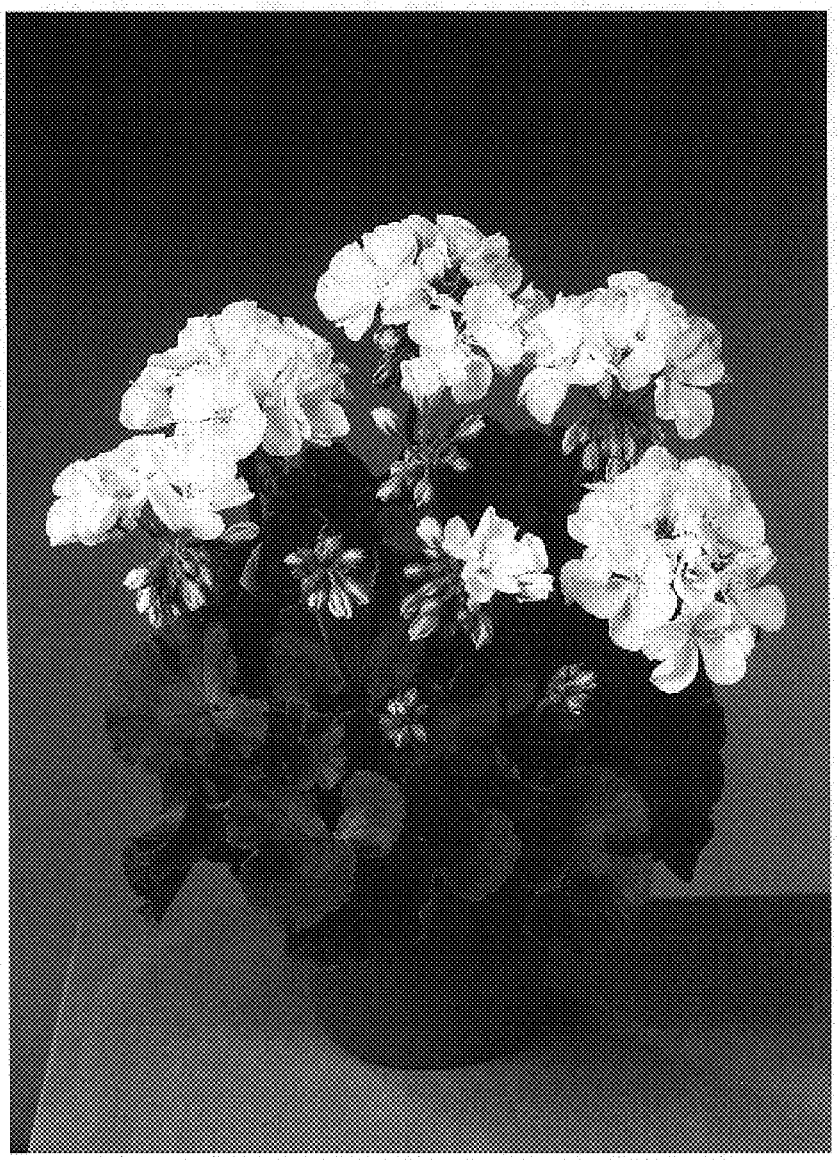

* * * * *